United States Patent [19]

Varco et al.

[11] Patent Number: 5,030,443
[45] Date of Patent: * Jul. 9, 1991

[54] ALGINATE HAIR SETTING COMPOSITIONS

[75] Inventors: Joseph Varco, Fairfield; Janusz Jachowicz, Bethel, both of Conn.

[73] Assignee: Clairol Incorporated, New York, N.Y.

[*] Notice: The portion of the term of this patent subsequent to Apr. 3, 2007 has been disclaimed.

[21] Appl. No.: 491,372

[22] Filed: Mar. 9, 1990

Related U.S. Application Data

[63] Continuation-in-part of Ser. No. 90,642, Aug. 28, 1987, Pat. No. 4,913,893.

[51] Int. Cl.$^5$ .............................................. A61K 7/06
[52] U.S. Cl. ...................................... 424/47; 424/70; 424/71
[58] Field of Search ................ 424/47, 70, 71, DIG. 1

[56] References Cited

U.S. PATENT DOCUMENTS 4,673,569 6/1987 Shernov et al. .............. 424/DIG. 1

FOREIGN PATENT DOCUMENTS 1017843 1/1964 United Kingdom .................. 424/71
1036497 7/1966 United Kingdom .................. 424/71

Primary Examiner—Thurman Page
Attorney, Agent, or Firm—Charles J. Zeller

[57] ABSTRACT

An aqueous hair setting composition having reduced tendency of flaking from the hair containing an alginate hair setting resin and a polymer having in a monomer unit at least one carboxylic acid moiety, said compositions preferably being in the form of an aerosol composition that produces a stable mousse upon delivery from the aerosol container.

19 Claims, No Drawings

ALGINATE HAIR SETTING COMPOSITIONS

This is a continuation-in-part application to U.S. Ser. No. 07/090,642 filed Aug. 28, 1987, now U.S. Pat. No. 4,913,893.

FIELD OF INVENTION

This invention concerns hair setting compositions incorporating alginates as the hair setting resin. More specifically, this invention relates to such hair setting compositions that contain, in addition to the alginate component, a polymeric component having at least one carboxylic acid group, the presence of the polymer in the composition beneficially reducing flaking off or powdering of the alginate after application of the composition to the hair of a consumer. Most specifically, the present invention concerns such hair setting compositions in the form of a mousse and that are suitable for delivery from an aerosol can.

BACKGROUND OF INVENTION

Formulas containing alginates are known in the prior art, as exemplified by GB 1,036,497 to Schwarzkopf. The Schwarzkopf compositions are primarily aqueous systems containing an alginate. Although a hair setting effect is obtained when such compositions are applied to hair and dried, the form of these prior art compositions makes them difficult and inconvenient to apply to the head. Thus, Schwarzkopf first prepares a first composition containing the alginate which has an acidic pH above 3.6. To use the composition, it is essential that the pH of the first composition be lowered to below 3.6, to cause precipitation of the alginate. The pH may be lowered in two ways. First, an acidic solution may be applied to the hair after application of the hair setting composition. Alternately, the pH of the first composition may be lowered to below 3.6 just prior to setting the hair by adding a dilute acid solution to the first composition.

Disadvantageously, Schwarzkopf's procedure requires a two-step operation because the complete hair setting composition comprising the mixture of the first composition and the acidifying solution is inherently unstable. Necessarily, the product of Schwarzkopf would be provided in kit form comprising the first composition and the acidifying solution. Use of the product entails careful measurement of each part to obtain the right proportions of ingredients, use preferably being performed by the trained personnel of a hair styling salon. Thus, the Schwarzkopf product is greatly limited in its ease of use.

GB 1,017,843 also to Schwarzkopf discloses a hair-fixing composition containing a modified gelatine as the setting agent, in lieu of the conventional film-forming agents such as shellac, alginates, carragenates, gelatine, dextrins, polyvinyl pyrrolidone or copolymers thereof with polyvinyl acetate, dimethyl hydantoin, formaldehyde resins and polymeric acrylic acid derivatives.

As indicated above, the use of alginates in hair setting compositions has not been exploited commercially because such compositions are not particularly stable. This would be especially true with ready-to-use compositions sold over the counter to retail customers. Thus, the alginate tends to precipitate from the ready-to-use compositions, requiring the use of a kit-type product as disclosed in Schwarzkopf '497.

More recently, hair setting compositions have taken the form of hair sprays that utilize synthetic polymers as the active ingredient. These compositions are generally prepared using alcohols as the principal vehicle. However, alginates, being intolerant to alcohols present at high concentrations, have not been used in such hairspray compositions. Accordingly, an aqueous vehicle or a hydroalcoholic vehicle having a low alcohol concentration must be employed in alginate hair setting compositions.

The problem of alginate instability is of greater concern in hair spray products, typically aerosol sprays, but also pump sprays. This is because alginate, if precipitated, clogs the valve of the spray nozzle. As a further disadvantage, when applied to hair, the alginate hair setting agent present in hair setting compositions tends to flake off. As a result, the consumer has the appearance of having dandruff.

Surprisingly, it has now been found that both the flaking problem and the stability problem can be largely alleviated by incorporating a polymer material having at least one carboxylic acid moiety into the hair setting composition.

SUMMARY OF THE INVENTION

It is object of the present invention to provide an alginate-containing hair setting composition in the form of a ready-to-use product, which does not require further end-user processing, either before, during or after use.

A primary object of the present invention is to incorporate an antiflaking agent, which agent is a polymer having at least one carboxylic acid moiety, into the hair setting composition.

A collateral benefit of the present invention is the ability to provide storage-stable alginate hair setting compositions, especially in a spray container form, typically an aerosol can.

These and other benefits and advantages of the present invention will be more fully understood upon reading the Detailed Disclosure of the Invention, a summary of which follows.

The ready-to-use compositions of the present invention contain an alginate usually in the form of salts or esters of alginic acid and an antiflaking agent in an amount effective to alleviate flaking or powdering of the alginate that has been applied to the hair. The antiflaking agent is a polymer that has one or more carboxylic acid groups in the monomer.

The alginate and antiflaking agent are contained in a vehicle that may include other hair treating actives compatible with the alginate and the antiflaking agent. The compositions of the present invention are preferably delivered in the form of a mousse. That is, the compositions are provided in a pressurized aerosol container, release of the compositions from the containers providing a stable aerated foam of the various constituents, which is applied directly to the hair of the user. However, the present compositions may also be in other ready-to-use forms, for example, lotions.

DETAILED DISCLOSURE OF THE INVENTION

The hair setting compositions of the present invention comprise an alginate, an antiflaking polymer agent having one or more carboxylic acid groups, and an aqueous vehicle for the alginate and polymer.

A number of alginates are known in the prior art which are useful for the purposes of this invention.

These alginates usually take the form of salts or esters of alginic acid, the preferred alginates being alkali metal or alkaline earth metal alginates and particularly sodium alginate. Illustrative of the alginates that may be employed in the present invention are sodium alginate, potassium alginate, ammonium alginate, propylene glycol alginate and ethylene glycol alginate.

A major drawback in the use of alginates as a hair setting resin is that the alginate, after it has been applied to hair, and during the time it remains on the hair, flakes or powders, giving the appearance of dandruff. Unexpectedly, it has been found that polymers having carboxylic acid moieties are suitable in greatly lessening this tendency of the alginate resin.

Suitable carboxylated polymers for use in the present invention are polyacrylic and polymethacrylic acids, and include such polymers crosslinked with polyfunctional agents such as allyl ethers of pentaerythritol or allyl esters of sucrose. The carboxylated polymers used herein are typically in their acid form, but may be partially neutralized, typically less than 50% neutralized. Generally they have a molecular weight of from about 1,000 to about 5 million, preferably from about 10,000 to about 1,000,000, most preferably from about 20,000 to about 500,000.

Commercially available polymers suitable in the present invention are Acrysols LMW and A-1 (Rohm and Haas); Carbopols 420, 430, 475 (Goodrich); Carbopols 910, 940 and 941 (polyacrylic acid cross-linked with allyl ethers of pentaerythritol, Carbopol 934 (polyacrylic acid crosslinked with allyl esters of sucrose and Carbopol 1342 (copolymers of acrylic acid and long chain alkyl methacrylate, crosslinked with allyl ethers of pentaerythritol).

The quantity of alginate present in the hair setting composition will vary depending upon the results desired and in the economics involved. Generally, the alginate is present in a concentration range of from about 0.1% to about 10% by weight based on the total weight of the hair setting composition, depending on the molecular weight of the alginate polymer. Alginate molecular weight is typically from about 5,000 to about 500,000, preferably from about 10,000 to about 250,000. In the preferred embodiment, the alginate constitutes from about 0.4 to about 3% by weight based on the total weight of the composition. As the molecular weight of the alginate increases, its quantity included in the composition decreases.

The antiflaking polymer is present in an amount effective to alleviate the flaking or powdering of the alginate after its application to hair. Generally, the amount of antiflaking polymer is from about 0.1 to about 10%, preferably from about 0.25 to about 3% by weight of the hair setting composition. The amount of antiflaking polymer is generally related to the amount of alginate contained in the composition. Thus, as the alginate level increases, the level of the antiflaking polymer likewise increases. The weight ratio of the alginate to the antiflaking agent is generally in the range of about 1:1 to about 5:1, preferably about 2:1 to about 3:1.

Surprisingly, the compositions of the present invention containing the carboxylated polymer are physically stable at an acidic pH above about 4. Accordingly, they may be manufactured, shipped and sold to consumers for use without further processing either before, during or after use. That is, the compositions are in ready-to-use form for the consumer. While the underlying reason for the stability is not clear, it appears that the antiflaking polymers are providing both enhanced stability and reduced flaking effects. Moreover, stability is obtained with a pH range at which excellent hair set retention is achieved.

By stable is meant that the composition exhibits essentially no precipitation of the alginate for at least one month at room temperature. Preferably, the compositions are stable for up to three months at room temperature. Such stability is critical for ready-to-use products, and especially for the aerosol and pump spray products of the present invention where container nozzles can become clogged.

The compositions of the present invention are suitable for use in the form of a lotion, but preferably are provided as an aerosol mousse. By lotion is meant a flowable composition having sufficient viscosity so that it is retained on the hair and without undue running down the side of the face or off the hair. When provided as an aerosol mousse, the compositions are provided in a pressurized container. Release of the composition from the container delivers the composition as a stable, aerated foam of the various constituents. Of course, the propellant largely dissipates from the foam to the atmosphere. By stable in this context is meant that the foam remains uncollapsed following delivery. Typically, the foam will remain in such state for above 2 minutes, preferably between about 5 to about 15 minutes.

In another form of the product, the composition may be provided in a pump spray container. However, in such form there is insufficient aerosolization to provide a foam. Rather, an atomized mist of the composition is delivered, and which may be applied directly to the hair of the user.

To formulate the present compositions as a mousse one or more foaming aids is incorporated in the composition. Illustrative of the foaming aids useful in the practice of the present invention are sodium, ammonium or triethanolamine lauryl sulfate; polyethylene glycol ether fatty alcohols (20–45 moles of ethoxylation), sodium isethionate, sodium lauroyl sarcosinate, and sodium and ammonium xylene sulphonate. Amphoteric surfactants such as lauramine oxide, cocamidopropyl hydroxysulfonate, betaines and the like can also be used. Pump spray products of the composition may also benefit from inclusion of the foaming aid, to provide a heavier mist.

The total quantity of foaming aids that may be incorporated in the hair setting composition of this invention will vary somewhat. Usually this will comprise about 0.1 to about 2.0% by weight based on the total weight of the hair setting composition, with the preferred range being from about 0.2 to about 1.0% on the same weight basis.

The aqueous carrier or vehicle for the composition of the present invention comprises water or a combination of water with other solvents. Solvents that may be employed along with the water to form the aqueous carrier are ethanol, isopropanol, and benzyl alcohol. The organic solvents typically comprise up to about 20% of the water-organic solvent system, preferably from about 5 to 15% of the solvent system.

In addition to the alginate and the antiflaking agent in the present composition, a number of adjuvants commonly found in hair setting preparations may also be incorporated therein. These are added to facilitate the application of the product, to provide chemical or physical stability or to improve the organoleptic properties of the product. These constituents are incorporated in the hair setting compositions of the present invention in an amount effective to provide their intended function, generally as noted below. By way of example of such adjuvants, mention may be made of (a) preservatives (methyl paraben, dibasic potassium phosphate, dibasic sodium phosphate, sodium benzoate, potassium sorbate, calcium propionate, sodium propionate, heximimum salts, 2-phenoxyethanol), within the range of 0.001 to 0.50%; (b) water-soluble and alginate-compatible synthetic or natural polymers (neutral, anionic or ampho-teric) employed for the improvement of film properties, viscosity adjustment, etc., such as poly(vinyl alcohol), poly(vinylpyrrolidone), poly(styrene sulphonate), carboxymethylcellulose, hydroxyethylcellulose, hydroxypropylcellulose, carboxymethylchitin, copolymers of methylvinyl ether and maleic anhydride and other high molecular weight compounds employed to plasticize the alginate film, within the range of 0.05 to 5%, (c) low molecular weight plasticizers such as propylene glycol, ethylene glycol, hexylene glycol, glycerol and triethanolamine, in the range of 0.05 to 3% and (d) other surfactants such as ethoxylated polysiloxanes (dimethicone copolyols) for the improvement of the tactile properties of polymer films and alkylamides such as or lauramides MEA or DEA as stabilizing agents for anionic surfactants, in the range of 0.05 to 2%.

In other aspects of the present invention, one or more hair treating actives may be incorporated with the composition in an effective amount. Thus, the utility of the compositions may be broadened by including a hair dye. Generally, the hair dye will be a direct dye capable of imparting a permanent, semipermanent or temporary color to hair. Typically, the dye would be present in an amount of from 0.05 to 5% by weight of the hair setting composition. A hair thickening ingredient, for example, polyvinyl pyrollidone and its copolymers, may also be incorporated. Typically, such agents would be present in an amount of from 0.05 to 5% by weight of the hair setting composition. Of course, the treating actives would need to be compatible with the constituent present in the compositions herein.

As indicated above, it is a preferred feature of the present invention to formulate the hair setting compositions of this invention as aerosol products to be dispensed from an aerosol can. For this purpose a propellent or propellant system is employed. A number of propellents used singularly or in combination well known in the aerosol art may be used for the present purposes. By way of example, mention may be made of hydroflurocarbon 152A ($CH_2CHF_2$), isobutane and dimethyl ether. The propellants may be used alone or in combination in various ratios. A particularly useful propellent system is a combination of hydroflurocarbon 152A and isobutane, preferably in the ratio of 80:20 to 60:40 of hydroflurocarbon 152A to isobutane.

In preparing the aerosol mousse products of this invention the hair setting composition and the propellent may be charged into the aerosol can in proportions that vary over range. These aerosols will generally comprise from about 3% to about 25% by weight propellant based on the total weight of the aerosol composition, the balance being made up by the hair setting composition. In the preferred form of this invention the aerosol mousse product will contain from about 3% to about 15% of propellant on the same weight basis.

The viscosity of the compositions of the present invention varies typically in the range of from about 10 to about 10,000 cps, preferably from about 20 to about 2,000 cps. The choice of viscosity depends on the concentration and molecular weight of the alginate and antiflaking agent, and the pH of the composition. The pH ranges from about 4 to about 6.5, preferably from 4 to about 5.

The mousse products of the present invention are evaluated for curl holding ability by their application to hair under controlled conditions. Curl relaxation is then measured on exposure to high humidity and compared with appropriate standards. For example, 0.3 g of mousse product is applied and spread throughout a 2 g swatch of hair. The hair tress is curled on a mandrel and dried at ambient conditions. Curl relaxation that consists of periodic measurement of the curl fall, is then performed under exposure to high humidity (90-95% R.H.).

The following examples are given to further illustrate the present invention. It is understood however that this invention is not limited thereto.

The procedure used in preparing the products shown in Examples 1-5 is the same. All the ingredients listed under the heading "Concentrate" are mixed together to form the hair setting composition. This Concentrate is then charged into an aerosol can which is sealed with a cover having a valve and valve stem assembly. The propellant is then introduced into the sealed can under pressure through the valve stem.

EXAMPLE 1

|  | % w/w |
|---|---|
| (A) Concentrate | |
| Sodium Alginate | 1.5 |
| Isosteareth 10 | 0.2 |
| Sodium isethionate | 0.25 |
| Methyl paraben | 0.10 |
| 2-Phenoxyethanol | 0.20 |
| Fragrance | q.s. |
| Deionized Water | q.s. to 100% |
| (B) Aerosol Composition | |
| Above concentrate | 92.0 |
| Hydroflurocarbon 152A/Isobutane (75:25) | 8.0 |

The performance of the product with a composition described above offers a long lasting hold effect to the hair as well as an excellent, nontacky film quality.

Examples 2-4 illustrate the use of alginates in combination with other water-soluble polymers.

EXAMPLE 2

|  | % w/w |
|---|---|
| (A) Concentrate | |
| Sodium Alginate | 0.75 |
| Gantrez 225* | 0.75 |
| Isosteareth 10 | 0.20 |
| Sodium isethionate | 0.25 |
| Methyl paraben | 0.10 |
| 2-Phenoxyethanol | 0.20 |
| Fragrance | q.s. |
| Deionized Water | q.s. 100% |
| (B) Aerosol Composition | |
| Above concentrate | 92.0 |
| Hydroflurocarbon 152A/Isobutane (75:25) | 8.0 |

*monoalkyl ester of Poly(methylvinylether/maleic acid)

|  | % w/w |
|---|---|
| (A) Concentrate | |

-continued

| | % w/w |
|---|---|
| Sodium Alginate | 0.75 |
| Poly(vinyl pyrrolidone) | 0.75 |
| Isosteareth 10 | 0.20 |
| Sodium isethionate | 0.25 |
| Methyl paraben | 0.10 |
| 2-Phenoxyethanol | 0.20 |
| Fragrance | q.s. |
| Deionized Water | q.s to 100% |
| (B) Aerosol Composition | |
| Above concentrate | 92.0 |
| Hydroflurocarbon 152A/Isobutane (75:25) | 8.0 |

| | % w/w |
|---|---|
| (A) Concentrate | |
| Sodium Alginate | 0.75 |
| Carboxymethylchitin | 0.75 |
| Isosteareth 10 | 0.20 |
| Sodium isethionate | 0.25 |
| Methyl paraben | 0.10 |
| 2-Phenoxyethanol | 0.20 |
| Fragrance | q.s. |
| Deionized Water | q.s. to 100% |
| (B) Aerosol Composition | |
| Above concentrate | 92.0 |
| Hydroflurocarbon 152A/Isobutane (75:25) | 8.0 |

Example 5 illustrates the use of propylene glycol alginate in a mousse composition.

EXAMPLE 5

| | % w/w |
|---|---|
| (A) Concentrate | |
| Propylene glycol alginate | 1.5 |
| Isosteareth 10 | 0.20 |
| Sodium isethionate | 0.25 |
| Methyl paraben | 0.1 |
| 2-Phenoxyethanol | 0.2 |
| Fragrance | q.s. |
| Deionized Water | q.s. to 100% |
| (B) Arosol Composition | |
| Above concentrate | 92.0 |
| Hydroflurocarbon 152A/Isobutane (75:25) | 8.0 |

EXAMPLE 6

The following aerosol mousse products were produced by first forming the Concentrate composition, filling an aerosol container with the Concentrate, and then pressurizing the container with propellant.

| | % w/w | |
|---|---|---|
| | A | B |
| (A) Concentrate | | |
| Sodium Alginate | 1.0 | 1.0 |
| Carbopol 941 (1) | 0.5 | — |
| Carbopol 1342 (2) | — | 0.5 |
| 2-Phenoxyethanol | 0.1 | 0.1 |
| Isosteareth-10 | 0.2 | 0.2 |
| Triethanolamine | 0.5 | 0.5 |
| Methyl paraben | 0.05 | 0.05 |
| D.I. Water | q.s. 100% | |
| (B) Aerosol Composition | | |
| Concentrate | 92.0 | 92.0 |
| Propellant (75/25 mixture of Hydrofluorocarbon 152A and butane) | 8.0 | 8.0 |

(1) Carbopol 941 is a crosslinked polyacrylic acid (B. F. Goodrich).
(2) Carbopol 1342 is a hydrophobically modified and crosslinked polyacrylic acid (B. F. Goodrich).

0.3 of each Aerosol Composition A and B was applied to a 6" long hair tress weighing 3 g. and worked in thoroughly by combing. The tresses $T_A$ and $T_B$, respectively, were permitted to dry and thereafter recombed. The film properties of the treatment were evaluated visually and by optical microscopy for each trees. Both trees $T_A$ and tress $T_B$ exhibited good adherence of the alginate film, with little evidence of flaking or powdering.

EXAMPLE 7

The following compositions were prepared, which compositions were not within the scope of the present invention.

| | % w/w | | | | | |
|---|---|---|---|---|---|---|
| | I | II | III | IV | V | VI |
| (A) Concentrate | | | | | | |
| Sodium alginate | 1.5 | 1.0 | 1.0 | 1.0 | 1.0 | 1.0 |
| Gantrez 225 (1) | — | 0.5 | — | — | — | — |
| Carboxymethyl-cellulose (2) | — | — | 0.5 | — | — | — |
| Carboxymethyl-chitin (3) | — | — | — | 0.5 | — | — |
| Amphomer (4) | — | — | — | — | 0.5 | — |
| Poly(vinyl pyrrolidone) (5) | — | — | — | — | — | 0.5 |
| 2-Phenoxyethanol | 0.1 | 0.1 | 0.1 | 0.1 | 0.1 | 0.1 |
| Isosteareth-10 | 0.2 | 0.2 | 0.2 | 0.2 | 0.2 | 0.2 |
| Methyl paraben | 0.05 | 0.05 | 0.05 | 0.05 | 0.05 | 0.05 |
| D.I. Water | q.s. 100% | | | | | |
| (B) Arosol Composition | | | | | | |
| Concentrate | 92.0 | | | | | |
| Propellant (75/25 mixture of Hydrofluorocarbon 152A and butane) | 8.0 | | | | | |

(1) Partial ethylester of the polycarboxylic recin formed from vinyl methyl ether and maleic anhydride (GAF Corp.)
(2) Carboxymethylcellulose (Dow Chemical)
(3) Carboxymethyl chitin (Atomergic Chemicals)
(4) Octylacrylamide/Acrylates/butylaminoethyl Methacrylate Copolymer (National Starch)
(5) Polyvinylpyrrolidone (GAF Corp.)

Aerosol Compositions I–VI were tested on hair in the same manner as Aerosol Compositions A and B of Example 6. Visual and optical microscopic observations showed excessive powdering. This was unexpected for the Aerosol Compositions II–IV containing the indicated polymers (1)–(5) because inclusion of such polymers in nonalginic hair setting compositions is known to suppress powdering. The flaking of Composition I was expected, in view of this known drawback in the use of alginates as a hair setting resin.

EXAMPLE 8

The Composition C identified below was prepared as a lotion, in accordance with the present invention.

| Component | Composition C (% w/w) |
|---|---|
| Sodium alginate | 1.0 |
| Poly(methacrylic acid) | 0.5 |

| Component | Composition C (% ww) |
|---|---|
| 2-Phenoxyethanol | 0.1 |
| Methyl paraban | 0.05 |
| D.I. Water | q.s. 100% |

The lotion Composition C was applied to hair. Visual and microscopic examination of the tress showed little flaking or powdering.

EXAMPLE 9

Tresses $T_A$ and $T_B$ were evaluated for the hair holding ability of the applied Aerosol Compositions A and B. Also tested in the same manner were tresses $T_I$, $T_{VII}$ and $T_{VIII}$ treated, respectively, with Aerosol Composition I and with Aerosol Compositions VII and VIII below, all of which are outside the scope of the present invention record. Composition VII contained chitosan lactate, which agent is known for its excellent hair set holding ability. Aerosol Composition VIII contained Polyquaternium 11, which polymer is also a known hair set holding resin.

|  | % w/w VII | VIII |
|---|---|---|
| (A) Concentrate |  |  |
| Isosteareth 10 | 0.1 | 0.05 |
| Chitosan lactate (1) | 1.25 | — |
| Polyquaternium 11 (2) | 4.0 | 7.0 |
| 2-Phenoxy ethanol | 0.1 | — |
| Sodium cocoylisethionate | 0.3 | 0.1 |
| Methyl paraben | 0.15 | 0.1 |
| D.I. Water | q.s. 100% |  |
| (B) Aerosol Composition |  |  |
| Concentrate | 92.0 | 92.0 |
| Propellant (75/25 mixture) of hydrofluorocarbon 152A and butane) | 8.0 | 8.0 |

(1) Prepared by combining Chitosan (Sea Cure/Protan Labs) with equivalent amount of lactic acid.
(2) Gafquat 755 manufactured by GAF.

In the results below, Holding Power (Hp) is the area under the set relaxation curve after 24 hours at 90% relative humidity using the procedure of Diaz, et al, *Set Relaxation of Human Hair*, J. Soc. Cosmet. Chem., 34:205-12 (1983).

| Tress | Hp (%/Hrs.) |
|---|---|
| $T_A$ | 1717 |
| $T_B$ | 1832 |
| $T_I$ | 1588 |
| $T_{VII}$ | 1500 |
| $T_{VIII}$ | 500 |

It is seen that Aerosol Compositions A and B are comparable to the Aerosol Composition VII containing a known, effective hair setting resin. The Aerosol Compositions A and I are also comparable in holding power, Aerosol Composition A exhibiting essentially no flaking compared to Aerosol Composition I. See Examples 6 and 7.

EXAMPLE 10

The Aerosol Composition below was prepared.

|  | % w/w |
|---|---|
| (A) Concentrate |  |
| Sodium alginate | 1.0 |
| Carbopol 1342 | 0.5 |
| 2-Phenoxyethanol | 0.1 |
| SD Alcohol | 10.0 |
| Igepan AC-78 | 0.05 |
| Citric acid | 0.05 |
| Methyl paraben | 0.05 |
| Fragrance | 0.10 |
| D.I. Water | q.s. 100% |
| (B) Products |  |
| Concentrate | 92.0 |
| Hydroflurocarbon 152A | 8.0 |

The citric acid was incorporated to obtain a pH of 4.5. The composition when applied to hair provided good set holding, had good tactile properties, and exhibited no flaking.

What is claimed is:

1. A hair setting composition for application to the hair of a user comprising from about 0.1 to about 10% of an alginate hair setting resin, from about 0.1 to about 10% of a polymer having at least one carboxylic acid moiety in a monomer unit, said polymer being effective to alleviate flaking of the composition from the hair following its application thereto, and from about 0.2 to about 80% of an aqueous vehicle, said composition being stable for a period of at least about one month at room temperature and during said period of stability being appliable directly to the hair of the user.

2. An aerosol composition contained in an aerosol can useful for setting hair comprising by weight of the aerosol composition from 75 to 97% of a hair setting composition and from 3 to 25% propellant, the hair setting composition containing by weight of the hair setting composition from about 0.1 to about 10% of an alginate hair setting resin, from about 0.1 to about 10% of a polymer having at least one carboxylic acid moiety in a monomer unit, said polymer being effective to alleviate flaking of the composition from the hair following its application thereto, from about 0.1 to about 2% of a foaming aid and an aqueous vehicle as the remainder of the hair setting composition, said aerosol composition being stable for a period of at least about one month at room temperature permitting thereby during said period of stability application of the composition directly to the hair of the user.

3. The composition of claim 1 or 2 wherein the alginate is an alkali metal alginate, ammonium alginate, ethylene or propylene glycol alginate.

4. The composition of claim 3 wherein the polymer is selected from the group consisting of polyacrylic acid, polymethacrylic acid, polyacrylic and polymethacylic acids crosslinked with a polyfunctional agent selected from the group consisting of allyl ethers of pentaerythritol, allyl esters of sucrose, and copolymers of acrylic acid with methacrylate crosslinked with allyl ethers of pentaerythritol, and their less than 50% partially neutralized salts.

5. The composition of claim 4 wherein said polymer is present in an amount of from about 0.25 to about 3% by weight of the hair setting composition.

6. The composition of claim 5 wherein said alginate is present in an amount of from about 0.4 to about 3% of said hair setting composition.

7. The composition of claim 6 wherein said alginate is sodium alginate.

8. The composition of claim 7 comprising from about 0.2 to about 1% foaming aid by weight of said hair setting composition.

9. The composition of claim 2 wherein said propellent system comprises from about 3.0 to about 15.0% of said aerosol composition.

10. The composition of claim 5 comprising by weight of the hair setting composition from about 0.4 to about 3% of said alginate, from about 0.2 to about 1% of said foaming aid, the aqueous vehicle including any adjuvants that may be present in the composition, the aerosol composition containing by weight of the aerosol composition from about 3.0 to about 15% propellent.

11. The composition of claim 10 wherein said alginate is an alkali metal alginate, ammonium alginate, ethylene or propylene glycol alginate.

12. A composition of claim 11 wherein said foaming aid is selected from the group consisting of sodium, ammonium or triethanolamine lauryl sulfate, polyethylene glycol ether fatty alcohols (20–45 moles of ethoxylation), sodium isethionate, sodium lauroyl sarcosinate, sodium or ammonium xylene sulphonate and mixtures thereof.

13. The composition of claim 11 wherein the polymer is an acrylic acid-long chain methacrylate copolymer crosslinked with allyl esters of pentaerythritol.

14. The composition of claim 12 wherein the alginate is sodium alginate.

15. The composition of claim 1 or 2 wherein the pH is from about 4 to about 6.5.

16. The composition of claim 10 wherein the composition has a pH in the range of 4–5.

17. The composition of claim 16 further comprising from 0.01 to about 0.1% of a low molecular weight carboxylic acid by weight of the hair setting composition.

18. The composition of claim 12 wherein the low molecular weight carboxylic acid is citric acid.

19. The composition of claim 18 wherein the acid is citric acid present in an amount of from about 0.01 to about 0.05% by weight of the hair setting composition.

* * * * *